United States Patent
Mori et al.

(10) Patent No.: US 9,703,202 B2
(45) Date of Patent: Jul. 11, 2017

(54) SURFACE TREATMENT PROCESS AND SURFACE TREATMENT LIQUID

(71) Applicant: TOKYO OHKA KOGYO CO., LTD., Kawasaki-shi (JP)

(72) Inventors: Daijiro Mori, Kanagawa (JP); Akira Kumazawa, Kanagawa (JP)

(73) Assignee: TOKYO OHKA KOGYO CO., LTD., Kawasaki-Shi (JP)

( * ) Notice: Subject to any disclaimer, the term of this patent is extended or adjusted under 35 U.S.C. 154(b) by 0 days.

(21) Appl. No.: 15/074,131

(22) Filed: Mar. 18, 2016

(65) Prior Publication Data

US 2016/0291477 A1 Oct. 6, 2016

(30) Foreign Application Priority Data

Mar. 31, 2015 (JP) ................................. 2015-073795
Nov. 18, 2015 (JP) ................................. 2015-225644

(51) Int. Cl.
| | | |
|---|---|---|
| G03F 7/40 | (2006.01) |
| H01L 21/3105 | (2006.01) |
| C08L 83/14 | (2006.01) |
| C07C 311/48 | (2006.01) |
| G03F 7/42 | (2006.01) |

(52) U.S. Cl.
CPC ............ *G03F 7/405* (2013.01); *C07C 311/48* (2013.01); *C08L 83/14* (2013.01); *G03F 7/422* (2013.01); *H01L 21/3105* (2013.01)

(58) Field of Classification Search
CPC ... G03F 7/11; G03F 7/40; G03F 7/405; C08L 83/14; H01L 21/3105; C07C 311/48
USPC ............................. 430/322, 325, 331; 564/82
See application file for complete search history.

(56) References Cited

U.S. PATENT DOCUMENTS

| | | | | |
|---|---|---|---|---|
| 4,400,509 A | * | 8/1983 | Bruynes ............... | C07D 499/00 540/226 |
| 4,828,764 A | * | 5/1989 | DesMarteau ........... | C07B 39/00 552/627 |
| 5,254,732 A | * | 10/1993 | Differding .............. | C07B 39/00 558/413 |
| 5,326,672 A | | 7/1994 | Tanaka et al. | |
| 5,707,783 A | * | 1/1998 | Stauffer .................. | G03F 7/265 430/286.1 |
| 7,514,204 B2 | * | 4/2009 | Hatakeyama ......... | G03F 7/0045 430/270.1 |
| 9,122,152 B2 | * | 9/2015 | Hatakeyama ........... | G03F 7/004 |
| 2004/0023515 A1 | * | 2/2004 | Gracias ............... | C23C 16/0272 438/782 |
| 2004/0202872 A1 | * | 10/2004 | Fang ....................... | C03C 17/30 428/447 |
| 2004/0265513 A1 | * | 12/2004 | Tamagawa ............... | B41M 5/41 428/32.21 |
| 2008/0038664 A1 | * | 2/2008 | Hamada ............... | C08G 77/045 430/270.1 |
| 2008/0241489 A1 | * | 10/2008 | Ishibashi ................... | G03F 7/11 428/199 |
| 2009/0281303 A1 | * | 11/2009 | Massonne ............... | C08B 15/05 536/56 |
| 2010/0028803 A1 | * | 2/2010 | Sugimoto ............. | G03F 7/0397 430/270.1 |
| 2011/0195190 A1 | | 8/2011 | Koshiyama et al. | |
| 2013/0255534 A1 | * | 10/2013 | Ryokawa .............. | H01L 23/296 106/2 |

FOREIGN PATENT DOCUMENTS

| | | |
|---|---|---|
| JP | H06-163391 | 6/1994 |
| JP | H07-142349 | 6/1995 |
| JP | 2010-129932 | 6/2010 |

* cited by examiner

*Primary Examiner* — Amanda C Walke
(74) *Attorney, Agent, or Firm* — Knobbe Martens Olson & Bear LLP

(57) ABSTRACT

A surface treatment liquid that can effectively prevent pattern collapse of, in particular, a silicon pattern and a surface treatment process using the surface treatment liquid. The surface treatment liquid contains a water repellent agent and an acid imide. The surface treatment process includes exposing a surface of a substrate to the surface treatment liquid to thereby hydrophobize the substrate surface.

10 Claims, No Drawings

SURFACE TREATMENT PROCESS AND SURFACE TREATMENT LIQUID

This application claims priority to Japanese Patent Application No. 2015-073795, filed Mar. 31, 2015; and Japanese Patent Application No. 2015-225644, filed Nov. 18, 2015, the contents of which are incorporated herein by reference.

BACKGROUND OF THE INVENTION

Field of the Invention

The present invention relates to a surface treatment process that is effective for preventing pattern collapse during formation of a fine pattern having a high aspect ratio, and relates to a surface treatment liquid that is used in the surface treatment process.

Related Art

In the production of semiconductor devices or other devices, lithography technology is used for treatment of substrates, such as etching. In this lithography technology, a photosensitive resin layer made of a photosensitive resin composition is formed on a substrate and is then selectively irradiated with and exposed to active radiation for development. Thereafter, the photosensitive resin layer is selectively removed by dissolution to form a resin pattern on the substrate. Subsequently, etching is performed using the resin pattern as a mask to form an etched pattern, such as a silicon pattern, on the substrate.

In recent years, the integration and miniaturization of semiconductor devices have been enhanced, and the refinement and increment of the aspect ratio in etched patterns have also advanced. However, such progress has simultaneously caused a problem so-called pattern collapse. Pattern collapse occurs when a large number of patterns are formed in parallel on a substrate and is a phenomenon in which adjacent patterns approach each other so as to lean on each other and, in some cases, causing breakage at the basal part or detaching of the pattern. Such pattern collapse may be an obstacle for production of a desired product, leading to a reduction in yield or reliability of the product.

It is known that the pattern collapse occurs during cleaning treatment after the formation of patterns by the surface tension of a cleaning liquid when the cleaning liquid is dried. In other words, when the cleaning liquid is removed during a drying procedure, stress based on the surface tension of the cleaning liquid is applied between the patterns to cause pattern collapse.

Accordingly, many approaches have been attempted for preventing pattern collapse by adding substances that decrease surface tension to cleaning liquids. For example, a cleaning liquid containing isopropyl alcohol and a cleaning liquid containing a fluorine-based surfactant have been proposed (e.g., Patent Documents 1 and 2). Alternatively, a surface treatment liquid containing a silylating agent and a solvent has been proposed (e.g., Patent Document 3).

Patent Document 1: Japanese Unexamined Patent Application, Publication No. H06-163391

Patent Document 2: Japanese Unexamined Patent Application, Publication No. H07-142349

Patent Document 3: Japanese Unexamined Patent Application, Publication No. 2010-129932

SUMMARY OF THE INVENTION

However, the use of the cleaning liquid or the surface treatment liquid designed in this way is unfortunately insufficient for preventing pattern collapse.

The present invention has been made in the light of the conventional circumstances described above, and it is an object of the invention to provide a surface treatment liquid capable of effectively preventing pattern collapse of, in particular, a silicon pattern (as used herein, the term "silicon pattern" encompasses not only a pattern made of a material containing Si but also a pattern made of a material containing $SiO_2$ and a pattern made of a material containing SiN) and to provide a surface treatment process using the surface treatment liquid.

The present inventors have diligently studied to solve the above-mentioned problems. As a result, the inventors have found that the above-mentioned problems can be solved by treating the surface of a pattern, such as a silicon pattern, with a surface treatment liquid containing a water repellent agent and an acid imide to hydrophobize the surface and increase the contact angle of a cleaning liquid, leading to the completion of the present invention. Specifically, the present invention provides the following.

A first aspect of the present invention is a surface treatment liquid comprising a water repellent agent and an acid imide.

A second aspect of the present invention is a surface treatment process of exposing the surface of the substrate to the surface treatment liquid of the first aspect to thereby hydrophobize the surface of a substrate.

The present invention can provide a surface treatment liquid capable of effectively preventing pattern collapse of, in particular, a silicon pattern and a surface treatment process using the surface treatment liquid.

DETAILED DESCRIPTION OF THE INVENTION

<<Surface Treatment Liquid>>

The surface treatment liquid according to the present invention will now be described.

The surface treatment liquid according to the present invention contains a water repellent agent and an acid imide. Each component will be described in detail hereafter.

<Acid Imide>

The acid imide used in this embodiment is a compound having a chemical structure formed by imidization of an acid such as a sulfonic acid, carboxylic acid, or phosphoric acid. That is, the acid imide has a structure represented by T-NR$^{43}$-T (each T represents an acid residue obtained by removing —OH from an acid, and R$^{43}$ represents a hydrogen atom, a halogen atom, or a monovalent organic group). When the acids are each, for example, a sulfonic acid represented by R$^{41}$—SO$_2$—OH or R$^{42}$—SO$_2$—OH (R$^{41}$ and R$^{42}$ are the same as those in a general formula (a1) described below), the acid residue represented by T-corresponds to the structure represented by R$^{42}$—SO$_2$— or R$^{42}$—SO$_2$—.

The acid imide used in this embodiment is preferably a compound having a chemical structure formed by imidization of a sulfonic acid. Specifically, the acid imide is preferably a sulfonimide compound represented by the general formula (a1):

$$R^{41}\text{—}SO_2\text{—}NR^{43}\text{—}SO_2\text{—}R^{42} \tag{a1}$$

wherein R$^{41}$ and R$^{42}$ may be the same or different and each represent a fluorine atom, a substituted or unsubstituted alkyl group, or a substituted or unsubstituted aromatic group and may together form a cyclic group; and R$^{43}$ is as described above, i.e., represents a hydrogen atom, a halogen atom, or a monovalent organic group.

Although $R^{A1}$ and $R^{A2}$ in the general formula (a1) may be the same or different, they are preferably the same.

The substituent optionally possessed by the alkyl group represented by $R^{A1}$ or $R^{A2}$ is not particularly limited and is preferably a hydrophobic group, more preferably a halogen atom such as a fluorine atom, and most preferably a fluorine atom. The substituted or unsubstituted alkyl group represented by $R^{A1}$ or $R^{A2}$ is not particularly limited and is preferably a substituted or unsubstituted linear or branched alkyl group having 1 to 10 carbon atoms, more preferably a substituted or unsubstituted linear or branched alkyl group having 1 to 8 carbon atoms, more preferably a substituted or unsubstituted linear or branched alkyl group having 1 to 4 carbon atoms, more preferably a substituted (i.e., having a substituent) linear or branched alkyl group having 1 to 4 carbon atoms, and most preferably a linear or branched alkyl group having 1 to 4 carbon atoms substituted with a hydrophobic group. The substituted linear or branched alkyl group having 1 to 4 carbon atoms represented by $R^{A1}$ or $R^{A2}$ is preferably a substituted alkyl group in which the hydrogen atoms of the alkyl group are partially or wholly substituted with hydrophobic groups, and more preferably a substituted alkyl group in which the hydrogen atoms of the alkyl group are wholly substituted with hydrophobic groups, wherein the hydrophobic groups are preferably halogen atoms such as fluorine atoms and are more preferably fluorine atoms, as described above.

The substituent optionally possessed by the aromatic group represented by $R^{A1}$ or $R^{A2}$ in the general formula (a1) is not particularly limited and is, for example, preferably a hydrophobic group, more preferably a halogen atom such as a fluorine atom, and most preferably a fluorine atom, as in the substituent optionally possessed by the alkyl group represented by $R^{A1}$ or $R^{A2}$. The substituted or unsubstituted aromatic group represented by $R^{A1}$ or $R^{A2}$ is not particularly limited and is preferably a substituted or unsubstituted aromatic group having 3 to 10 carbon atoms, more preferably a substituted or unsubstituted aromatic group having 5 to 7 carbon atoms, more preferably a substituted or unsubstituted aryl group having 5 to 7 carbon atoms, and most preferably a substituted or unsubstituted phenyl group. The substituted (i.e., having a substituent) aromatic group represented by $R^{A1}$ or $R^{A2}$ is preferably a substituted aromatic group in which the hydrogen atoms of the aromatic group are partially or wholly substituted with hydrophobic groups, and more preferably a substituted aromatic group in which the hydrogen atoms of the aromatic group are wholly substituted with hydrophobic groups, wherein the hydrophobic groups are preferably halogen atoms such as fluorine atoms and are more preferably fluorine atoms. The substituted aromatic group represented by $R^{A1}$ or $R^{A2}$ is preferably a perfluoroaryl group having 3 to 10 carbon atoms in which the hydrogen atoms of the aryl group are wholly substituted with fluorine atoms, more preferably a perfluoroaryl group having 5 to 7 carbon atoms, and most preferably a perfluorophenyl group.

Particularly, $R^{A1}$ and $R^{A2}$ in the general formula (a1) are each preferably a fluorine atom or a substituted or unsubstituted alkyl group, and more preferably a substituted or unsubstituted alkyl group, wherein the substituted or unsubstituted alkyl group is preferably that mentioned above.

The sulfonimide compound represented by the general formula (a1) is preferably a compound in which $R^{A1}$ and $R^{A2}$ are each a substituted or unsubstituted linear or branched alkyl group having 1 to 4 carbon atoms, wherein $R^{A1}$ and $R^{A2}$ may together form a cyclic group, and $R^{A3}$ is a hydrogen atom; and more preferably a compound in which $R^{A1}$ and $R^{A2}$ are each a linear or branched perfluoroalkyl group having 1 to 4 carbon atoms, wherein $R^{A1}$ and $R^{A2}$ may together form a cyclic group, and $R^{A3}$ is a hydrogen atom.

In the general formula (a1), $R^{A1}$ and $R^{A2}$ may together form a cyclic group. The sulfonimide compound having such a cyclic group is preferably, for example, a sulfonimide cyclic compound represented by a general formula (a2):

(a2)

wherein $R^{A4}$ represents a substituted or unsubstituted alkylene group or a substituted or unsubstituted divalent aromatic group, and $R^{A3}$ is as described above.

$R^{A4}$ in the general formula (a2) preferably represents a substituted or unsubstituted alkylene group, more preferably a substituted or unsubstituted linear or branched alkylene group having 1 to 10 carbon atoms, more preferably a substituted or unsubstituted linear or branched alkylene group having 1 to 8 carbon atoms, more preferably a substituted or unsubstituted linear or branched alkylene group having 1 to 4 carbon atoms, and most preferably a substituted or unsubstituted linear alkylene group having 1 to 4 carbon atoms, in particular, a substituted linear alkylene group having 1 to 4 carbon atoms.

$R^{A3}$ in the general formula (a2) is the same as that in the general formula (a1) and preferably represents a hydrogen atom or a halogen atom and more preferably a hydrogen atom.

The sulfonimide cyclic compound represented by the general formula (a2) is preferably a compound in which $R^{A4}$ represents a substituted or unsubstituted linear alkylene group having 1 to 4 carbon atoms and $R^{A3}$ represents a hydrogen atom or a halogen atom and is more preferably a compound in which $R^{A4}$ represents a linear perfluoroalkylene group having 1 to 4 carbon atoms and $R^{A3}$ represents a hydrogen atom.

The amount of the acid imide in the surface treatment liquid of this embodiment is preferably 0.03 to 10 mass %, more preferably 0.05 to 8 mass %, and most preferably 0.08 to 6 mass % based on the total mass of the surface treatment liquid. Within this range, the surface treatment liquid can sufficiently enhance the hydrophobicity of the surface of a substrate and can secure the application properties thereof. Herein, the surface of a substrate as an object to which hydrophobicity is applied may include a pattern surface, such as a silicon pattern, formed on the substrate (as used herein, this may be simply referred to as "substrate surface").

In the surface treatment liquid containing an acid imide of this embodiment, provision of water repellency by the water repellent agent is enhanced. Although the mechanism of action is not clear, it is presumed that the acid imide functions as a proton donor or an electron donor to promote the reaction between the water repellent agent and the substrate surface.

<Water Repellent Agent>

The water repellent agent is not particularly limited and may be a conventionally known water repellent agent, preferably, a silylating agent.

The silylating agent is preferably a silicon compound having a trialkylsilyl group, specifically, a trialkylsilyl group represented by $R^{S1}R^{S2}R^{S3}Si-$ in the following general formula (s2) and more preferably a silicon compound represented by the general formula (s2) (as used herein, this may be simply referred to as "silicon compound"),

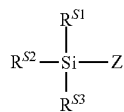
(s2)

wherein $R^{S1}$, $R^{S2}$, and $R^{S3}$ may be the same or different and each represents an alkyl groups; and Z represents an alkoxy group, an amino group, an alkylamino group, a trialkylsilylamino group, a halogen atom, or a nitrogen-containing heterocyclic group, wherein the nitrogen-containing heterocyclic group contains the nitrogen atom directly bonded to Si in the general formula (s2) as a ring-constituting atom.

$R^{S1}$, $R^{S2}$, and $R^{S3}$ in Formula (s2) may be either the same or different, and are preferably the same.

The alkyl group represented by $R^{S1}$, $R^{S2}$, or $R^{S3}$ is not particularly limited, and is preferably a linear or branched alkyl group having 1 to 10 carbon atoms, more preferably a linear or branched alkyl group having 1 to 5 carbon atoms, more preferably a linear or branched alkyl group having 1 to 3 carbon atoms, more preferably a methyl group or an ethyl group, and most preferably a methyl group.

Z in the general formula (s2) preferably represents an alkoxy group, an alkylamino group, a trialkylsilylamino group, or a nitrogen-containing heterocyclic group containing the nitrogen atom directly bonded to Si in the general formula (s2) as a ring-constituting atom, and more preferably an alkylamino group, a trialkylsilylamino group, or the nitrogen-containing heterocyclic group.

The alkoxy group represented by Z in the general formula (s2) is not particularly limited, and is preferably a linear or branched alkoxy group having 1 to 10 carbon atoms, more preferably a linear or branched alkoxy group having 1 to 5 carbon atoms, and more preferably a linear or branched alkoxy group having 1 to 3 carbon atoms, in particular, such as a methoxy group and an ethoxy group.

The alkylamino group represented by Z in the general formula (s2) may be any of monoalkylamino groups and dialkylamino groups and is preferably a dialkylamino group. The alkyl group of the dialkylamino group is not particularly limited and is preferably a linear or branched alkyl group having 1 to 10 carbon atoms, more preferably a linear or branched alkyl group having 1 to 5 carbon atoms, more preferably a linear or branched alkyl group having 1 to 3 carbon atoms, more preferably a methyl group or an ethyl group, and most preferably a methyl group. Each alkyl group of the dialkylamino group is preferably the same as that represented by $R^{S1}$, $R^{S2}$, or $R^{S3}$ in the general formula (s2). The two alkyl groups of the dialkylamino group may be the same or different and are preferably the same.

The trialkylsilylamino group represented by Z in the general formula (s2) is preferably a group including, as the alkyl group, a linear or branched alkyl group having 1 to 10 carbon atoms, more preferably a group including a linear or branched alkyl group having 1 to 5 carbon atoms, more preferably a group including a linear or branched alkyl group having 1 to 3 carbon atoms, more preferably a group including a methyl group or an ethyl group, and most preferably a group including a methyl group.

The trialkylsilylamino group represented by Z is preferably a group in which atoms bonded to the nitrogen atom forming the amino group are hydrogen atoms only, except for the trialkylsilyl group.

The trialkylsilyl group of the trialkylsilylamino group represented by Z is preferably the same group as that represented by $R^{S1}R^{S2}R^{S3}Si-$ in the general formula (s2).

The nitrogen-containing heterocyclic group represented by Z in the general formula (s2) is a heterocyclic group containing the nitrogen atom directly bonded to Si in the general formula (s2) as a ring-constituting atom. Such a heterocyclic group is preferably a heterocyclic group in which the hetero atom as a ring-constituting atom is a nitrogen atom, an oxygen atom, or a sulfur atom, more preferably a heterocyclic group in which the hetero atom is a nitrogen atom, more preferably a heterocyclic group containing 1 to 3 nitrogen atoms as the hetero atoms, more preferably a heterocyclic group containing two nitrogen atoms as the hetero atoms, and most preferably an imidazole ring. Here, when Z represents a heterocyclic group containing nitrogen atoms as the hetero atoms forming the ring, at least one of the nitrogen atoms directly bonds to Si in the general formula (s2).

The halogen atom represented by Z in the general formula (s2) can be a fluorine atom, a chlorine atom, an iodine atom, or a bromine atom, and a fluorine atom and a chlorine atom are preferred.

The silicon compound is preferably a compound in which Z in the general formula (s2) represents a nitrogen-containing heterocycle containing the nitrogen atom directly bonded to Si in the general formula (s2) as a ring-constituting atom, and more preferably a compound in which $R^{S1}$, $R^{S2}$, and $R^{S3}$ in the general formula (s2) each represents a linear or branched alkyl group having 1 to 3 carbon atoms.

Specifically, the silicon compound is a silylating agent, for example, represented by any of the following formulae (1) to (3):

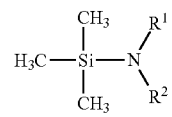
(1)

wherein $R^1$ represents a hydrogen atom or a saturated or unsaturated alkyl group; and $R^2$ represents a saturated or unsaturated alkyl group, a saturated or unsaturated cycloalkyl group, or a saturated or unsaturated heterocycloalkyl group; and $R^1$ and $R^2$ may bond to each other to form a saturated or unsaturated heterocycloalkyl group containing a nitrogen atom,

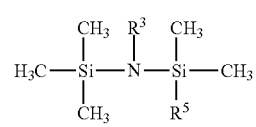
(2)

wherein $R^3$ represents a hydrogen atom, a methyl group, a trimethylsilyl group, or a dimethylsilyl group; and $R^4$ and $R^5$ each independently represents a hydrogen atom, an alkyl group, or a vinyl group,

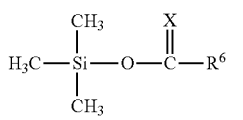

(3)

wherein X represents O, CHR$^7$, CHOR$^7$, CR$^7$R$^7$, or NR$^8$; R$^6$ and R$^7$ each independently represents a hydrogen atom, a saturated or unsaturated alkyl group, a saturated or unsaturated cycloalkyl group, a trialkylsilyl group, a trialkylsiloxy group, an alkoxy group, a phenyl group, a phenethyl group, or an acetyl group; and R$^8$ represents a hydrogen atom, an alkyl group, or a trialkylsilyl group.

The saturated or unsaturated heterocycloalkyl group containing a nitrogen atom formed by bonding of R$^1$ and R$^2$ in the formula (1) may be a heteroaryl group (where the hetero atom is the nitrogen atom). Examples of the silylating agent represented by the formula (1) include N,N-dimethylaminotrimethylsilane, N,N-diethylaminotrimethylsilane, t-butylaminotrimethylsilane, allylaminotrimethylsilane, trimethylsilyl acetamide, trimethylsilyl piperidine, trimethylsilyl imidazole, trimethylsilyl morpholine, 3-trimethylsilyl-2-oxazolidinone, trimethylsilyl pyrazole, trimethylsilyl pyrrolidine, 2-trimethylsilyl-1,2,3-triazole, and 1-trimethylsilyl-1, 2,4-triazole.

Examples of the silylating agent represented by the formula (2) include hexamethyldisilazane, N-methylhexamethyldisilazane, 1,2-di-N-octyltetramethyldisilazane, 1,2-divinyltetramethyldisilazane, heptamethyldisilazane, nonamethyltrisilazane, and tris(dimethylsilyl)amine.

Examples of the silylating agent represented by the formula (3) include trimethylsilyl acetate, trimethylsilyl propionate, trimethylsilyl butyrate, and trimethylsilyloxy-3-penten-2-one.

Among these silylating agents, N,N-dimethylaminotrimethylsilane (TMSDMA) and hexamethyldisilazane (HMDS) are preferred from the viewpoint of further enhancing the hydrophobicity.

It is also preferred to use methoxytrimethylsilane or trimethylsilyl imidazole, which is also used in Examples described below, as the silicon compound. In particular, trimethylsilyl imidazole is high in substrate surface-hydrophobizing effect and can achieve hydrophobization with a small amount thereof.

The surface treatment liquid of this embodiment may contain a single water repellent agent or two or more water repellent agents mixed together.

The content of the water repellent agent is preferably 0.1 to 99.97 mass %, more preferably 0.1 to 99.95 mass %, more preferably 0.1 to 50 mass %, more preferably 0.5 to 30 mass %, more preferably 1 to 20 mass %, and most preferably 1 to 10 mass %, based on the total mass of the surface treatment liquid of the embodiment. When the surface treatment liquid does not contain any solvent, the content of the water repellent agent is preferably 80 to 99.97 mass %; the lower limit is preferably 92 mass %, more preferably 94 mass %, and most preferably 98 mass %; and the upper limit may be 99.95 mass %. When the surface treatment liquid contains a solvent, the content of the water repellent agent is preferably 0.1 to 50 mass %; the lower limit is preferably 0.5 mass % and more preferably 1 mass %; and the upper limit is preferably 30 mass %, more preferably 20 mass %, and most preferably 10 mass %. Within this range, the surface treatment liquid can sufficiently enhance the hydrophobicity of the surface of a substrate and can secure the application properties thereof.

<Solvent>

The surface treatment liquid of this embodiment preferably further contains a solvent. When the water repellent agent used is a silylating agent represented by the formula (s2), such as methoxytrimethylsilane, or a silylating agent represented by the formula (2), such as hexamethyldisilazane (HMDS), the surface treatment liquid may contain a solvent or may not contain any solvent.

Any conventionally known solvent that can dissolve the water repellent agent and does not substantially damage the substrate surface as an object to be treated can be used.

The solvent contained in the surface treatment liquid of the embodiment is not particularly limited. Examples of the solvent include glycol monoethers, such as ethylene glycol monomethyl ether, ethylene glycol monoethyl ether, ethylene glycol monopropyl ether, ethylene glycol monobutyl ether, propylene glycol monomethyl ether, propylene glycol monoethyl ether, propylene glycol monopropyl ether, propylene glycol monobutyl ether, diethylene glycol monomethyl ether, diethylene glycol monoethyl ether, diethylene glycol monopropyl ether, and diethylene glycol monophenyl ether; glycol diethers, such as ethylene glycol dimethyl ether, ethylene glycol diethyl ether, ethylene glycol dipropyl ether, propylene glycol dimethyl ether, propylene glycol diethyl ether, propylene glycol dipropyl ether, diethylene glycol dimethyl ether, diethylene glycol diethyl ether, and diethylene glycol dipropyl ether; glycol monoacetates, such as ethylene glycol monomethyl ether acetate, ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, and diethylene glycol monoethyl ether acetate; monoether monoacetates of diols, such as diethylene glycol monopropyl ether acetate, diethylene glycol monobutyl ether acetate, diethylene glycol monophenyl ether acetate, propylene glycol monomethyl ether acetate, propylene glycol monoethyl ether acetate, propylene glycol monopropyl ether acetate, 2-methoxybutyl acetate, 3-methoxybutyl acetate, 4-methoxybutyl acetate, 2-methyl-3-methoxybutyl acetate, 3-methyl-3-methoxybutyl acetate, 3-ethyl-3-methoxybutyl acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, and 4-methyl-4-methoxypentyl acetate; ketones, such as acetone, methyl ethyl ketone, diethyl ketone, methyl isobutyl ketone, ethyl isobutyl ketone, and cyclohexanone; esters, such as methyl propionate, ethyl propionate, propyl propionate, isopropyl propionate, methyl 2-hydroxypropionate, ethyl 2-hydroxypropionate, ethyl 2-hydroxy-2-methylpropionate, methyl 3-methoxypropionate, ethyl 3-methoxypropionate, ethyl 3-ethoxypropionate, ethyl 3-propoxypropionate, propyl 3-methoxypropionate, isopropyl 3-methoxypropionate, ethyl ethoxyacetate, ethyl oxyacetate, methyl 2-hydroxy-3-methylbutanoate, methyl acetate, ethyl acetate, propyl acetate, isopropyl acetate, butyl acetate, isoamyl acetate, methyl carbonate, ethyl carbonate, propyl carbonate, butyl carbonate, methyl pyruvate, ethyl pyruvate, propyl pyruvate, butyl pyruvate, methyl acetoacetate, ethyl acetoacetate, benzyl acetate, ethyl benzoate, diethyl oxalate, diethyl maleate, and γ-butyrolactone; ethers, such as diethyl ether, dipropyl ether, dibutyl ether, dihexyl ether, benzyl methyl ether, benzyl ethyl ether, and tetrahydrofuran; aromatic compounds, such as benzene, toluene, xylene, ethylbenzene, cresol, and chlorobenzene; aliphatic alcohols, such as methanol, ethanol, n-propanol, isopropanol, n-butanol, n-hexanol, and cyclohexanol; glycols, such as ethylene glycol, diethylene glycol, propylene glycol, and dipropylene glycol; glycerol; and aprotonic polar organic solvents, such as N,N,N',N'-tetramethylurea, N-methyl-2-pyrrolidone, N,N-dimethylformamide, N,N-dimethylacetamide, hexamethylphosphoramide, 1,3-dimethyl-2-imidazolidinone, and dimethyl sulfoxide.

The solvent may be a hydrocarbon solvent such as an aliphatic hydrocarbon (e.g., n-hexane, cyclohexane, n-heptane, n-octane, n-nonane, methyloctane, n-decane, n-undecane, or n-dodecane) or may be a terpene solvent such as menthane (e.g., p-menthane, o-menthane, or m-menthane), diphenylmenthane, limonene, terpinene (e.g., α-terpinene, β-terpinene, or γ-terpinene), bornane, norbornane, pinane, pinene (e.g., α-pinene or β-pinene), Calan, a monoterpene (e.g., longifolene), or a diterpene (e.g., abietane).

Among these solvents, aprotonic solvents can satisfactorily maintain the activity of the water repellent agent and are therefore preferred, and mono ether monoacetates of diols, aliphatic alcohols, and esters are preferred from the viewpoint of the surface treatment effect and replaceability with a cleaning liquid. These solvents may be used alone or in a combination of two or more thereof.

<<Surface Treatment Process>>

The surface treatment process according to the present invention will now be described.

The surface treatment process according to the present invention hydrophobizes a surface of a substrate by exposing the surface of the substrate to the surface treatment liquid of the present invention.

The substrate used in the embodiment is not particularly limited and is preferably a substrate including at least one selected from the group consisting of silicon, silicon oxide, silicon nitride, titanium nitride, and tungsten at least on the surface. Among these substrates, silicon, silicon oxide, and silicon nitride show more satisfactory effects of the present invention and are therefore more preferred.

A surface of the substrate used in the embodiment may be etched. Hereinafter, the pattern formed by etching a surface of a substrate is also referred to as "etched pattern".

The etched pattern is not particularly limited and is, for example, a pattern formed by etching a substrate using a resin pattern as a mask.

The substrate surface may be exposed to a surface treatment liquid by any known method. Examples of the method include a method in which the surface treatment liquid is vaporized into vapor, and the vapor is brought into contact with the substrate surface; and a method in which the surface treatment liquid containing a silylating agent is brought into contact with the substrate surface by, for example, spraying, spin coating, dip coating, or roll coating.

The time for the exposure of the substrate surface to the surface treatment liquid is preferably 1 to 60 seconds. The contact angle of water on the surface is preferably increased to 40° to 120°, more preferably to 60° to 100°, after the surface treatment.

In this embodiment, if the organic solvent or other components contained in the surface treatment liquid remains on the substrate surface after the exposure of the substrate surface to the surface treatment liquid, such a residue is preferably removed. The method for removing the residue is not particularly limited. For example, the residue can be removed by blowing a gas, such as nitrogen or dried air, to the substrate surface; by heating the substrate to an appropriate temperature according to the boiling point of the solvent to be removed; or by cleaning the substrate surface with a conventionally known cleaning liquid (e.g., water, isopropyl alcohol, surfactant rinse, SPM, or APM) that has been used in cleaning treatment.

In terms of throughput, the surface treatment and the cleaning treatment for removing the residue are preferably performed successively. Accordingly, the surface treatment liquid is preferably selected so as to have excellent replaceability with the cleaning liquid.

In the surface treatment process of the embodiment, when the water repellent agent is a silylating agent, dehydration condensation of the hydroxyl groups generated by hydrolysis of the silylating agent can form a coating film (thin film) containing the silicon compound on the substrate surface, and the coating film can hydrophobize the substrate surface. The surface treatment process of the embodiment can hydrophobize the substrate surface.

Accordingly, hydrophobization of the surface can prevent, for example, a substrate provided with a fine pattern on the surface from pattern collapse.

The surface treatment liquid and surface treatment process of the embodiment have excellent effects of providing hydrophobicity to, in particular, silicon, silicon oxide, silicon nitride, and etched patterns thereof.

In recent years, integration and miniaturization of semiconductor devices have been enhanced, and refinement and increment of the aspect ratio in organic patterns, such as silicon patterns, have also advanced. However, such progress has simultaneously caused a problem: so-called pattern collapse. Pattern collapse occurs when a large number of inorganic patterns are formed in parallel on a substrate and is a phenomenon in which adjacent patterns approach each other so as to lean on each other and, in some cases, causing breakage of the pattern at the basal part. The occurrence of such pattern collapse prevents a desired product from being produced, leading to a reduction in yield or reliability of the product.

It is known that pattern collapse occurs during rinse treatment after the formation of patterns by the surface tension of the rinsing liquid when the rinsing liquid is dried. That is, when a rinsing liquid is removed during a drying procedure, stress based on the surface tension of the rinsing liquid is applied between the patterns to cause pattern collapse.

Herein, the force F applied between inorganic patterns during the drying procedure after rinsing is represented by the following Expression (I):

$$F = 2\gamma \cdot \cos\theta \cdot A/D,$$

wherein γ represents the surface tension of a rinsing liquid; θ represents the contact angle of the rinsing liquid; A represents the aspect ratio of inorganic patterns; and D represents the distance between the side walls of the inorganic patterns.

Accordingly, provision of water repellency to the surfaces of inorganic patterns and an increase in the contact angle of a rinsing liquid (a reduction in the value of case) can reduce the force acting between the inorganic patterns during the drying procedure after rinsing and thus prevent pattern collapse.

Examples

The present invention will now be described in detail with reference to examples. The present invention is not limited to the following examples.

In the examples, any of the following acid imides 1 to 3 was used. In comparative examples, such acid imides were not used, or trifluoromethanesulfonic acid was used instead of the acid imides.

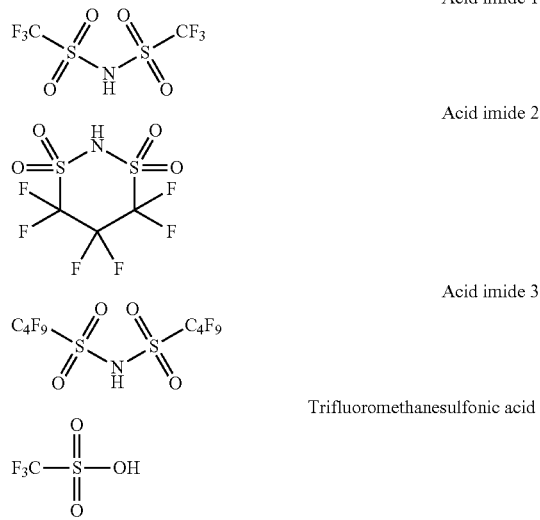

Acid imide 1

Acid imide 2

Acid imide 3

Trifluoromethanesulfonic acid

The silylating agents used in examples and comparative examples were the following N,N-dimethylaminotrimethylsilane (TMSDMA), methoxytrimethylsilane, hexamethyldisilazane (HMDS), and/or trimethylsilyl imidazole (TMS-imidazole).

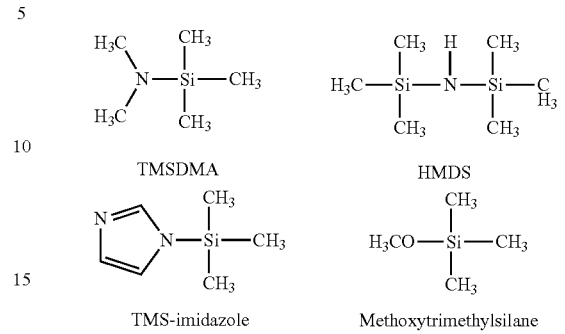

TMSDMA

HMDS

TMS-imidazole

Methoxytrimethylsilane

The solvents used in examples and comparative examples were as follows:
Propylene glycol monomethyl ether acetate (PM),
Butyl acetate, and
Methanol (MeOH).

[Examples of Preparation of Surface Treatment Liquid]

Surface treatment liquids were prepared using additives, such as silylating agents, solvents, and acid imides, in the types and amounts shown in Tables 1 and 2. The unit of the amount of each component shown in Tables 1 and 2 is part(s) by mass.

TABLE 1

| | Chemical composition | | | | | | Contact angle (°) | | | | | |
| --- | --- | --- | --- | --- | --- | --- | --- | --- | --- | --- | --- | --- |
| | | | | | | | Si | | Th—Ox | | SiN | |
| | Silylating agent | Amount | Solvent | Amount | Additive | Amount | 10 sec | 60 sec | 10 sec | 60 sec | 10 sec | 60 sec |
| Comparative Example 1 | TMSDMA | 5 | PM | 95 | — | — | 80.1 | 84.5 | 73.0 | 79.3 | 59.5 | 67.5 |
| Example 1 | TMSDMA | 5 | PM | 94.9 | Acid imide1 | 0.1 | 80.9 | 87.8 | 76.2 | 83.8 | 65.6 | 73.0 |
| Example 2 | TMSDMA | 5 | PM | 94.5 | Acid imide 1 | 0.5 (0.0018 mol) | 85.0 | 90.2 | 80.8 | 91.2 | 67.8 | 74.9 |
| Example 3 | TMSDMA | 5 | PM | 90 | Acid imide 1 | 5 | 84.4 | 89.0 | 82.3 | 87.4 | 70.3 | 74.6 |
| Comparative Example 2 | HMDS | 5 | PM | 95 | — | — | 51.8 | 72.5 | 30.1 | 49.3 | 16.2 | 29.9 |
| Example 4 | HMDS | 5 | PM | 94.5 | Acid imide 1 | 0.5 | 82.2 | 84.3 | 75.8 | 82.8 | 62.8 | 66.9 |
| Comparative Example 3 | HMDS + TMS-imidazole | 2.5/2.5 | PM | 95 | — | — | 88.5 | 91.0 | 83.2 | 90.0 | 69.6 | 75.8 |
| Example 5 | HMDS + TMS-imidazole | 2.5/2.5 | PM | 94.5 | Acid imide 1 | 0.5 | 89.5 | 92.0 | 89.9 | 91.5 | 78.5 | 83.2 |
| Comparative Example 4 | TMSDMA | 5 | Butyl acetate | 95 | — | — | 80.5 | 82.6 | 75.7 | 80.8 | 62.9 | 70.7 |
| Example 6 | TMSDMA | 5 | Butyl acetate | 94.5 | Acid imide 1 | 0.5 | 85.3 | 91.2 | 81.3 | 86.1 | 70.3 | 76.2 |
| Example 7 | TMSDMA | 5 | PM | 94.5 | Acid imide 2 | 0.5 | 84.5 | 89.7 | 81.6 | 88.2 | 65.1 | 71.7 |
| Example 8 | TMSDMA | 5 | PM | 94.5 | Acid imide 3 | 0.5 | 85.1 | 91.2 | 81.9 | 89.8 | 66.3 | 71.0 |
| Comparative Example 5 | TMSDMA | 5 | PM | 94.73 | Trifluoro methanesulfonic acid | 0.27 (0.0018 mol) | 82.8 | 89.4 | 77.6 | 90.1 | 64.7 | 72.7 |

TABLE 2

| | Chemical composition | | | | | | Contact angle (°) | | | | | |
| | | | | | | | Si | | Th—Ox | | SiN | |
| | Silylating agent | Amount | Solvent | Amount | Additive | Amount | 10 sec | 60 sec | 10 sec | 60 sec | 10 sec | 60 sec |
| --- | --- | --- | --- | --- | --- | --- | --- | --- | --- | --- | --- | --- |
| Comparative Example 6 | TMS-imidazole | 5 | PM | 95 | — | — | 88.0 | 91.1 | 83.5 | 90.1 | 68.0 | 76.5 |
| Example 9 | TMS-imidazole | 5 | PM | 94.5 | Acid imide 1 | 0.1 | 91.0 | 92.0 | 90.0 | 91.1 | 75.8 | 82.0 |
| Comparative Example 7 | HMDS | 100 | — | — | — | — | 65.3 | 76.1 | 59.5 | 73.3 | 32.7 | 58.0 |
| Example 10 | HMDS | 99.9 | — | — | Acid imide 1 | 0.5 | 80.5 | 90.8 | 81.1 | 91.7 | 64.9 | 79.6 |
| Comparative Example 8 | Methoxytrimethylsilane | 5 | PM | 95 | — | — | 68.2 | 72.5 | 4.5 | 4.6 | 23.5 | 22.3 |
| Example 11 | HMDS + TMS-imidazole | 5 | PM | 94.5 | Acid imide 1 | 0.5 | 70.4 | 79.2 | 51.0 | 60.7 | 24.1 | 28.9 |
| Comparative Example 9 | Methoxytrimethylsilane | 5 | MeOH | 95 | — | — | 72.1 | 70.6 | 4.2 | 4.6 | 5.1 | 4.4 |
| Example 12 | Methoxytrimethylsilane | 5 | MeOH | 94.5 | Acid imide 1 | 0.5 | 78.4 | 82.2 | 48.2 | 54.5 | 10.0 | 12.6 |
| Comparative Example 10 | Methoxytrimethylsilane | 100 | — | — | — | 0.5 | 68.2 | 69.0 | 5.1 | 4.7 | 23.4 | 27.2 |
| Example 13 | Methoxytrimethylsilane | 99.5 | — | — | Acid imide 1 | 0.5 | 78.0 | 80.9 | 68.4 | 71.8 | 48.2 | 57.0 |

[Verification of Hydrophobization Effect]

The substrate used was a silicon substrate (Si), SiO$_2$ substrate (Th-Ox), or silicon nitride substrate (SiN) (each substrate having a size of 2 cm×3 cm) as shown in Tables 1 and 2. The substrate was immersed in an aqueous solution of 1% hydrogen fluoride at 25° C. for 1 minute, was washed with running pure water at room temperature, and was then dried by nitrogen blow for 1 minute. The substrate was thus pretreated.

The contact angles before the pretreatment were 74.1° in the case of Si, 5.9° in the case of SiO$_2$, and 31.8° in the case of SiN.

The pretreated substrates were respectively immersed in the surface treatment liquids shown in Tables 1 and 2 for the time shown in Tables 1 and 2, were then immersed in isopropyl alcohol for 1 minute, were washed with running water, and were dried with N$_2$ blow.

A drop of pure water (1.5 µL) was placed onto the surface of each substrate (wafer), and the contact angle was measured with Dropmaster 700 (manufactured by Kyowa Interface Science Co., Ltd.). The results are shown in Tables 1 and 2.

The results shown in Tables 1 and 2 demonstrated that the hydrophobicity of the surface of each substrate was enhanced by treatment with a surface treatment liquid containing an acid imide. Accordingly, the contact angle of a cleaning liquid is increased by at least performing surface treatment of etched patterns with this surface treatment liquid, which probably weakens the force acting between the patterns during the drying and effectively prevents pattern collapse.

Comparison of the results of Examples 2, 4, 5, 9, and 11 with, respectively, those of Comparative Examples 1, 2, 3, 6, and 8 demonstrated that a surface treatment liquid containing an acid imide had an excellent effect of providing hydrophobicity to a substrate surface, regardless of the type of the silylating agent.

It was also demonstrated that when the silylating agent used was N,N-dimethylaminotrimethylsilane (TMSDMA), hexamethyldisilazane (HMDS), trimethylsilyl imidazole, or a combination of at least two or more thereof, the effect of providing hydrophobicity to a substrate surface was particularly excellent.

The results of Examples 1 to 3 demonstrated that a surface treatment liquid containing an acid imide had an excellent effect of providing hydrophobicity to a substrate surface, regardless of the amount of the acid imide.

Comparison of the results of Examples 5, 7, and 8 with those of Comparative Example 1 demonstrated that a surface treatment liquid containing an acid imide had an excellent effect of providing hydrophobicity to a substrate surface, regardless of the type of the acid imide.

Comparison of the results of Examples 2, 6, and 12 with, respectively, those of Comparative Examples 1, 4, and 9 demonstrated that a surface treatment liquid containing an acid imide had an excellent effect of providing hydrophobicity to a substrate surface, regardless of the type of the solvent.

Comparison of the results of Examples 10 and 13 with, respectively, those of Comparative Examples 7 and 10 demonstrated that a surface treatment liquid containing an acid imide had an excellent effect of providing hydrophobicity to a substrate surface, even if no solvent was used.

Comparison of the results of Example 2 with those of Comparative Example 5, where the molar amount of acid imide 1 used in Example 2 was the same as that of trifluoromethanesulfonic acid used in Comparative Example 5, demonstrated that the surface treatment liquid containing acid imide 1 of Example 2 had a higher effect of providing hydrophobicity to a substrate surface than the effect of the surface treatment liquid containing trifluoromethanesulfonic acid of Comparative Example 5.

What is claimed is:

1. A surface treatment liquid comprising a water repellent agent and an acid imide, wherein the water repellent agent is a silylating agent.

2. The surface treatment liquid according to claim 1, wherein the acid imide is a sulfonimide compound represented by the general formula (a1):

$$R^{41}\text{—}SO_2\text{—}NR^{43}\text{—}SO_2\text{—}R^{42} \quad (a1)$$

wherein $R^{41}$ and $R^{42}$ are the same or different, each represents a fluorine atom, a substituted or unsubstituted alkyl group, or a substituted or unsubstituted aromatic group, and optionally together form a cyclic group; and $R^{43}$ represents a hydrogen atom, a halogen atom, or a monovalent organic group.

3. The surface treatment liquid according to claim 2, wherein the sulfonimide compound is a sulfonimide cyclic compound represented by the following general formula (a2):

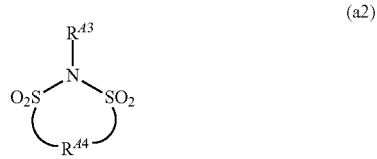

wherein $R^{A4}$ represents a substituted or unsubstituted alkylene group or a substituted or unsubstituted divalent aromatic group, and $R^{A3}$ represents a hydrogen atom, a halogen atom, or a monovalent organic group.

4. The surface treatment liquid according to claim 2, wherein the acid imide compound is at least one selected from the group consisting of acid imide 1, acid imide 2, and acid imide 3 represented by the following formulas:

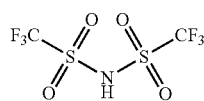

Acid imide 1

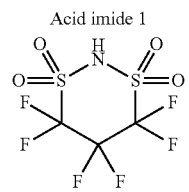

Acid imide 2

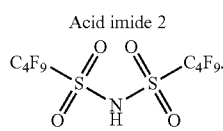

Acid imide 3

5. The surface treatment liquid according to claim 1, wherein the silylating agent comprises a silicon compound represented by the general formula (s2):

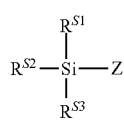

wherein $R^{S1}$, $R^{S2}$, and $R^{S3}$ are the same or different and each represents an alkyl group; and Z represents an alkoxy group, an amino group, an alkylamino group, a trialkylsilylamino group, a halogen atom, or a nitrogen-containing heterocyclic group, wherein the nitrogen-containing heterocyclic group contains a nitrogen atom directly bonded to Si in the general formula (s2) as a ring-constituting atom.

6. The surface treatment liquid according to claim 5, wherein Z in the silicon compound represented by the general formula (s2) is the nitrogen-containing heterocyclic ring.

7. The surface treatment liquid according to claim 1, wherein the silylating agent is at least one selected from the silylating agents each represented by the following general formulae (1) to (3):

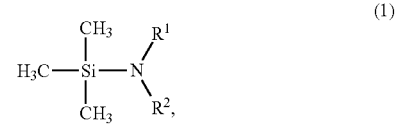

wherein $R^1$ represents a hydrogen atom or a saturated or unsaturated alkyl group; and $R^2$ represents a saturated or unsaturated alkyl group, a saturated or unsaturated cycloalkyl group, or a saturated or unsaturated heterocycloalkyl group; and $R^1$ and $R^2$ may bond to each other to form a saturated or unsaturated heterocycloalkyl group containing a nitrogen atom,

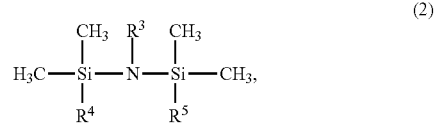

wherein $R^3$ represents a hydrogen atom, a methyl group, a trimethylsilyl group, or a dimethylsilyl group; and $R^4$ and $R^5$ each independently represents a hydrogen atom, a methyl group, an alkyl group, or a vinyl group,

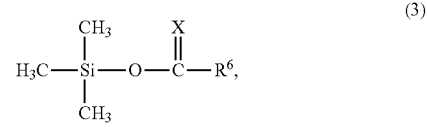

wherein X represents O, $CHR^7$, $CHOR^7$, $CR^7R^7$, or $NR^8$; $R^6$ and $R^7$ each independently represents a hydrogen atom, a saturated or unsaturated alkyl group, a saturated or unsaturated cycloalkyl group, a trialkylsilyl group, a trialkylsiloxy group, an alkoxy group, a phenyl group, a phenethyl group, or an acetyl group; and $R^8$ represents a hydrogen atom, an alkyl group, or a trialkylsilyl group.

8. The surface treatment liquid according to claim 1, wherein the silylating agent is at least one selected from the group consisting of N,N-dimethylaminotrimethylsilane (TMSDMA), methoxytrimethyl silane, hexamethyldisilazane (HMDS), and trimethyl silyl imidazole (TMS-imidazole) each represented by the following formulae:

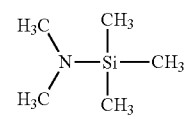

TMSDMA

-continued

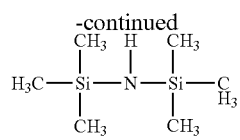

HMDS

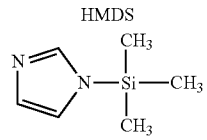

TMS-imidazole

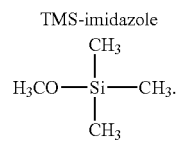

Methoxytrimethylsilane

9. A surface treatment process comprising exposing a surface of a substrate to the surface treatment liquid according to claim 1 to thereby hydrophobize the surface of the substrate.

10. The surface treatment liquid according to claim 5, wherein, Z in the silicon compound represented by the general formula (s2) is the nitrogen-containing heterocyclic ring and the nitrogen-containing heterocyclic ring contains a nitrogen atom directly bonded to Si in the general formula (s2) as a ring-constituting atom.

\* \* \* \* \*